United States Patent [19]

Chou

[11] 4,329,239
[45] May 11, 1982

[54] HYDROCARBYL DIHYDROURACIL, ITS METHOD OF PREPARATION AND LUBRICATING OIL COMPOSITION CONTAINING SAME

[75] Inventor: Kechia J. Chou, Wappingers Falls, N.Y.

[73] Assignee: Texaco Inc., White Plains, N.Y.

[21] Appl. No.: 149,222

[22] Filed: May 12, 1980

[51] Int. Cl.³ ............................................. C10M 1/32
[52] U.S. Cl. .............................. 252/51.5 A; 544/309; 544/312
[58] Field of Search .................... 252/51.5 A, 47.5; 544/309, 312

[56] References Cited

U.S. PATENT DOCUMENTS

| | | | |
|---|---|---|---|
| 3,137,698 | 6/1964 | Pfister | 544/309 |
| 3,187,005 | 6/1965 | Slezak | 252/51.5 A X |
| 3,360,523 | 12/1967 | Loux | 544/309 X |
| 3,422,108 | 1/1969 | Adams et al. | 544/309 |
| 3,796,663 | 3/1974 | Hotten | 252/51.5 A |
| 4,081,386 | 3/1978 | Sowerby | 252/51.5 A X |
| 4,120,804 | 10/1978 | Smith et al. | 252/51.5 A X |
| 4,194,982 | 3/1980 | Chou | 252/47.5 |

OTHER PUBLICATIONS

Fahmy et al., Bulletin of the Chemical Society of Japan, vol. 50 (No. 10), pp. 2678–2681 (1977).

Primary Examiner—Andrew Metz
Attorney, Agent, or Firm—Carl G. Ries; Robert A. Kulason; James J. O'Loughlin

[57] ABSTRACT

A hydrocarbyl-substituted dihydrouracil represented by the formula:

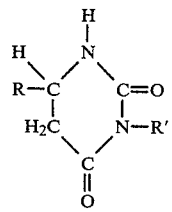

in which R is a hydrocarbyl radical having an average molecular weight ranging from about 150 to 2000 and R' is hydrogen, a hydrocarbyl radical having from 1 to 20 carbon atoms, or an R''—(X—R''')$_y$— radical in which R'' is an alkyl radical having from 1 to 12 carbon atoms, X is oxygen or an —NH— radical, R''' is a divalent hydrocarbon radical having from 1 to 3 carbon atoms and y is an integer from 1 to 3, a method for preparing said hydrocarbyl-substituted dihydrouracil, and a lubricating oil composition containing same is provided.

21 Claims, No Drawings

HYDROCARBYL DIHYDROURACIL, ITS METHOD OF PREPARATION AND LUBRICATING OIL COMPOSITION CONTAINING SAME

BACKGROUND OF THE INVENTION

1. Field of the Invention

This invention lies in the field of art relating to a lubricating oil composition adapted for use between a plurality of moving surfaces with which the fluid composition is in contact for the purpose of reducing the friction between these surfaces and to provide protection from wear and corrosion. These lubricant compositions tend to deteriorate under conditions of use with the attendant formation of sludge, lacquer and carbonaceous or resinous materials which adhere to the engine parts, particularly the piston rings, grooves and skirts, and cyclinder walls thus reducing the operating efficiency of the engine. To counteract the formation of these deposits, and/or to ameliorate the effects of such deposits, certain chemical additives have been found, which when added to a lubricating oil, have the ability to minimize the formation of the deposits or to maintain the deposits formed suspended in the oil so that the engine is kept clean and in efficient operating condition for extended periods of time. These agents are known in the art to which this invention pertains as detergents, dispersants or detergent-dispersants. Metal organic compounds are particularly useful in this respect and are exemplified by the oil-soluble zinc, calcium and barium salts of petroleum sulfonic acids, alkylated hydroxy benzoic acids, dialkyl dithiophosphoric acids and the like.

There are drawbacks associated with the use of organic metal salts in a lubricating oil composition for an internal combustion engine. A major drawback is that the metal salts formed by neutralization of the acids resulting from the combustion process are generally insoluble in the lubricating oil composition. More importantly, these insoluble metal salts occur as hard deposits on the piston rings, piston skirts or the cylinder liners and in the groove of the engine. These hard deposits are believed to be a major contributor to the wear that is experienced in an internal combustion engine. This problem is particularly acute with compression ignition engines, such as diesel engines, wherein the engine oil is subjected to extremely high temperature and compression stresses.

It is an object of the present invention to provide a new class of compounds which are useful as additives in lubricating oil compositions.

It is another object to provide an improved lubricating oil composition for an internal combustion engine.

It is a further object to provide a deposits-modifying additive for lubricants which is effective for reducing engine wear.

It is another object to provide a lubricating oil composition useful in diesel engines.

2. Description of the Prior Art

U.S. Pat. No. 3,796,663 discloses the preparation and use of an N-hydroxy hydrocarbyl-substituted succinimide in a lubricating oil composition.

U.S. Pat. No. 4,104,182 discloses N-alkoxy hydrocarbyl succinimides as deposit modifiers for lubricating oil compositions.

A copending application, Ser. No. 149,223 filed on May 12, 1980 discloses hydrocarbyl carbamidopropanamide and their preparation and use.

The disclosures of the above are incorporated herein by reference.

SUMMARY OF THE INVENTION

The novel hydrocarbyl-substituted dihydrouracil compound of this invention is represented by the formula:

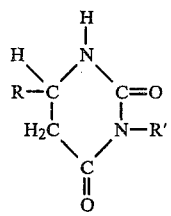

in which R is a hydrocarbyl radical having an average molecular weight ranging from about 150 to 2000 and R' is hydrogen, a hydrocarbyl radical having from 1 to 20 carbon atoms or a R''—(X—R''')$_y$—radical in which R'' is an alkyl radical having from 1 to 12 carbon atoms, X is oxygen or an —NH— radical, R''' is a divalent hydrocarbon radical having from 1 to 3 carbon atoms and y is an integer from 1 to 3. The novel process of the invention for preparing the noted dihydrouracil involves a two-step reaction between equimolar amounts of N-hydroxyhydrocarbyl succinimide and an amine. The N-hydroxyhydrocarbyl succinimide is initially reacted with p-toluene-sulfonyl chloride in the presence of a base to form an intermediate reaction product followed by a reaction with a suitable amine to produce the noted dihydrouracil.

A novel lubricating oil composition is also provided comprising a base oil of lubricating viscosity and the above described dihydrouracil.

DESCRIPTION OF THE PREFERRED EMBODIMENTS

The hydrocarbyl-substituted dihydrouracil compound of the invention is represented by the formula:

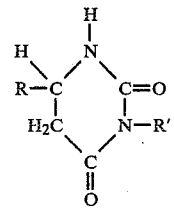

in which R is a hydrocarbyl radical having an average molecular weight (MW) ranging from about 150 to 2000 and R' is hydrogen, a hydrocarbyl radical having from 1 to 20 carbon atoms, or an R''—(X—R''')$_y$— radical in which R'' is an alkyl radical having from 1 to 12 carbon atoms, X is oxygen or an —NH— radical, R''' is a divalent hydrocarbon radical having from 1 to 3 carbon atoms and y is an integer from 1 to 3. A more preferred dihydrouracil of the invention comprises the compound in which the hydrocarbyl radical has a molecular weight ranging from about 150 to 1400. An effective dihydrouracil compound of the invention also comprises a dihydrouracil compound in which the hydrocarbyl radical has an average molecular weight ranging from about 800 to 1400.

A particularly preferred class of hydrocarbyl-substituted dihydrouracils are those in which the hydrocarbyl radical is an alkenyl or polyalkenyl radical. Typically, the alkenyl or polyalkenyl radical is one which has been derived through the polymerization of a low molecular weight olefin, such as ethylene, propylene, 1-butene, 2-butene and isobutylene or a mixture of low molecular weight olefins to produce a polyolefin having an average molecular weight corresponding to the molecular weight of the hydrocarbyl radical "R". A particularly preferred polyalkenyl radical is one derived from isobutylene to produce a polyisobutenyl radical having a molecular weight within the molecular weight ranges prescribed hereinabove. An effective polyalkenyl radical can be prepared by copolymerizing a mixture of ethylene and propylene by known methods. The average molecular weight of hydrocarbyl, alkenyl or polyalkyl radical represented by R is determined by vapor phase osmometry.

The R' substituent in the prescribed dihydrouracil is hydrogen, a hydrocarbyl radical having from 1 to 20 carbon atoms or an R''—(X—R''')$_y$— radical in which R'' is an alkyl radical having from 1 to 12 carbon atoms, X is oxygen or an —NH— radical, R''' is a divalent hydrocarbon radical having from 1 to 3 carbon atoms and y is an integer from 1 to 3. The hydrocarbyl radical herein can be an aliphatic, cycloaliphatic, aromatic, alkaryl or aralkyl radical. A preferred hydrocarbyl radical is one having from 1 to 12 carbon atoms. A particularly preferred hydrocarbyl radical is an aromatic or alkaryl radical having from 6 to 10 carbon atoms. Examples of suitable hydrocarbyl radicals include phenyl, tolyl, benzyl, isobutyl, 2-ethylhexyl, methyl, ethyl, propyl, decyl, dodecyl, tetradecyl, octadecyl and hexadecyl.

The hydrocarbyl-substituted dihydrouracil of the invention is produced in a two-step process. The starting reactant employed is an N-hydroxy hydrocarbyl-substituted succinimide represented by the formula:

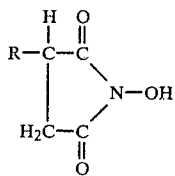

in which R is a hydrocarbyl radical having an average molecular weight ranging from 150 to 2000. The hydrocarbyl radical represented by R in the starting reactant corresponds to the above defined hydrocarbyl radical in the hydrocarbyl-substituted dihydrouracil compound of the invention.

The N-hydroxy hydrocarbyl-substituted succinimide is reacted with p-toluene sulfonyl chloride on an equimolar basis in the presence of a solvent and a base or acid acceptor, such as pyridine. The reaction can be conducted at a temperature ranging from about 0° C. to 10° C. Desirably, the reaction vessel is cooled in an ice-water bath to control the rate of reaction. On completion of this reaction, an intermediate addition reaction product of the succinimide and the p-toluene sulfonyl chloride is produced accompanied by splitting off of hydrogen chloride. This intermediate reaction is depicted by the following formula:

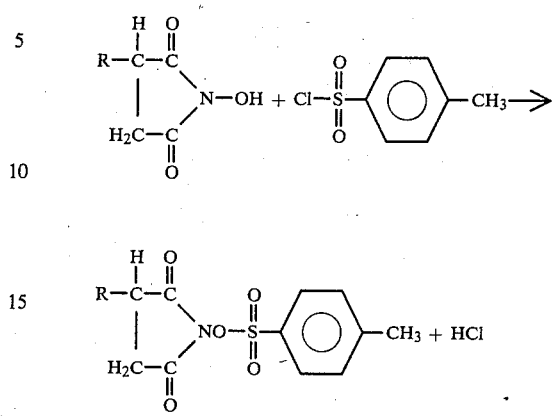

In the second step of the reaction, the intermediate reaction product is reacted with a compound having a primary amine function in equimolar amounts with said primary amine radical. The mole ratio of the reactants in this reaction is critical with respect to said primary amine in order to produce the prescribed hydrocarbyl-substituted dihydrouracil. Thus, it is essential that a 1:1 mole ratio of the intermediate reaction product and of the primary amine be employed with no excess of the primary amine. Secondary amines are generally not effective for producing dihydrouracils. A secondary amine functional group within the chemical structure of a primary amine reactant does not change the essential mole ratios required for this process.

The primary amine reactant employed in the second step of the reaction is represented by the formula:

R'NH$_2$ in which R' is a hydrogen, a hydrocarbyl radical having from 1 to 20 carbon atoms or an R''(X—R''')$_y$— radical in which R'' is an alkyl radical having from 1 to 12 carbon atoms, X is oxygen or an —NH— radical, R''' is a divalent hydrocarbyl radical having from 1 to 3 carbon atoms and y is an integer from 1 to 3. The hydrocarbyl radical can be an alkyl, aryl, cycloaliphatic, alkaryl or aralkyl radical such as phenyl, tolyl, benzyl, methyl, ethyl, isobutyl, decyl, octadecyl and hexadecyl radicals.

The primary amine reactant is added directly to the reaction mixture containing the intermediate reaction product. This reaction can be conducted at a temperature ranging from about 0° to 100° C. Generally, the reaction mixture is allowed to warm up to room temperature and then heated to its reflux temperature and maintained at this temperature for about an hour. The final product mixture is cooled, water washed, dried, filtered and the solvent removed to yield the hydrocarbyl-substituted dihydrouracil of the invention.

The following examples illustrate the practice of this invention.

EXAMPLE 1

3-Phenyl-6-Tetrapropenyl-5,6-Dihydrouracil

A mixture of N-hydroxytetrapropenyl succinimide (107 mmol), 200 mls. of ethyl ether and 40 mls. of pyridine is stirred in an ice-water bath. 107 mmol of p- toluenesulfonyl chloride is added while the mixing is continued. After 15 minutes, 107 mmol of aniline is introduced. The reaction mixture is cooled, washed with 300 mls. of water and is then dried over anhydrous magnesium sulfate. The dried mixture is filtered and the solvent is removed using a water aspirator. 31 grams of a viscous product are recovered. Infrared analysis peaks at 3333 cm$^1$, and 1750 cm$^1$ and a mass spectrum analysis of 356 indicated that the material was 3-phenyl-6-tetrapropenyl-5,6-dihydrouracil.

3-phenyl-6-polyisobutenyl-(1290 MW)-5,6-dihydrouracil

A mixture of 138 grams of polyisobutenyl N-hydroxy succinimide derived from Indopol H-300 having an effective molecular weight of 1290 and hydroxylamine, 300 mls. of heptane and 20 mls. of pyridine is stirred in an ice-water bath. Sixty-five mmols of p-toluenesulfonyl chloride is added with continued mixing. After 15 minute, 65 mmols of aniline is introduced. The reaction mixture is then allowed to graually warm to room temperature after which it is heated to reflux and refluxed for one hour. A precipitate is formed and is filtered off. The filtrate is washed with 500 mls. of methanol. The heptane solvent is removed by water aspirator to yield 124 grams of a viscous dark brown product. Infrared analysis peaks at 3290 cm$^{-1}$ and 1742 cm$^1$ indicate that the material is 3-phenyl-6-polyisobuteneyl-(1290 mw)-5,6-dihydrouracil.

EXAMPLE 3

3-decyloxypropylaminopropyl-6-polyisobutenyl-(1290 MW)-5,6-dihydrouracil

A mixture of 138 grams of polyisobutenyl (1290 mw) N-hydroxy succinimide, 300 mls. of heptane and 20 mls. of pyridine is stirred in an ice-water bath. Sixty-five mmols of p-toluenesulfonyl chloride is added with continued mixing. After 15 minutes, 65 mmols of decyloxypropylaminopropylamine is introduced. The reaction mixture is then allowed to gradually warm to room temperature after which it is heated to reflux and refluxed for an hour. The mixture is filtered and the filtrate is washed with 500 mls. of methanol. The heptane solvent is removed by aspiration to yield 141 grams of product. Infrared analysis peaks at 3402 cm$^{-1}$ and 1751 cm$^{-1}$ indicate that the material is 3-decyloxypropylaminopropyl-6-polyisobutenyl-(1290 mw)-5,6-dihydrouracil.

EXAMPLE 4

3-dodecyloxypropyl-6-polyisobutenyl-(1290 MW)-5,6-dihydrouracil

A mixture of 138 grams of N-hydroxypolyisobutenyl (1290 MW) succinimide, 300 mls. of heptane and 20 mls. of pyridine is stirred in an ice-water bath. Sixty-five mmols of p-toluenesulfonyl chloride is added with continued mixing. After 15 minutes, 65 mmols of decyloxypropylamine is introduced. The reaction mixture is then allowed to gradually warm to room temperature after which it is heated to reflux and refluxed for one hour. The mixture is filtered and the filtrate is washed with 500 mls. of methanol. The heptane solvent is aspirated off to yield 136 grams of product. Infrared analysis peaks at 3402 cm$^1$ and 1751 cm$^{-1}$ indicate that the material is 3-decyloxypropyl-6-polyisobutenyl-(1290 mw)-5,6-dihydrouracil.

Specific examples of other hydrocarbyl-substituted dihydrouracil compounds of this invention include 3-phenyl-6-polyisobutenyl (1290 mw)-5,6-dihydrouracil, 3-phenyl-6-polyisobutenyl (900 mw)-5,6-dihydrouracil, 3-phenyl-6-polyisobutenyl (300 mw)-5,6-dihydrouracil, 3-phenyl-6-polyisobutenyl (2000 mw)-5,6-dihydrouracil, 3-phenyl-6-hydrocarbyl (1500 mw)-5,6-dihydrouracil, 3-phenyl-6-hydrocarbyl (1200 mw)-5,6-dihyrouracil, 3-phenyl-6-pentapropenyl-5,6-dihydrouracil, 3-phenyl-6-tetraisobutenyl-5,6-dihydrouracil, 3-phenyl-6-pentaisobutenyl-5,6-dihydrouracil, 3-phenyl-6-ethylene-propylene copolymer (800 mw)-5,6-dihydrouracil, 3-phenyl-6-ethylene-propylene copolymer (1200 mw)-5,6-dihydrouracil, 3-dodecyl-6-tetrapropenyl-5,6-dihydrouracil, 3-octadecyl-6-tetrapropenyl 5,6-dihydrouracil and 3-tetradecyl-6-polyisobutenyl-(1300 mw)-5,6-dihydrouracil.

The additive of the invention can be employed in a mineral or synthetic base oil of lubricating viscosity or in a lubricating oil composition. The hydrocarbon mineral base oil can be a paraffinic base, naphthene base or mixed paraffin-naphthene base distillate or residual oil. Paraffin base distillate lubricating oil fractions are preferred for the formulation of the highest quality engine motor oils. The lubricating oil base will generally have been subjected to solvent refining to improve its lubricity and viscosity temperature relationship as well as to solvent dewaxing to remove waxy components and to improve the pour of the oil. Generally, mineral lubricating oils having an SUS viscosity at 100° F. between 50 and 1000 can be used in the preparation of oil composition of the invention with the preferred base oils having a viscosity range from 70 to 300 SUS at 100° F. A blend of base oils can be employed to provide a suitable base oil for either a single or multigrade motor oil.

Other lubricating oil bases can be employed such as synthetic hydrocarbon oils obtained by the polymerization of olefins as well as synthetic lubricating oils of the alkylene oxide type of the mono- and polycarboxylic acid ester type, such as the acids of adipic acid, sebasic acid and azelaic acid.

The additive of the invention can be employed in oil compositions and lubricating oils or concentrates therefor in concentrations ranging from 0.01 to about 50 percent by weight. A blended lubricating oil composition will generally contain from about 0.1 to about 5 percent by weight of the additive with the preferred concentrations ranging from 0.2 to 3 percent by weight. In addition, the lubricating oil composition may contain other lubricating oil additives such as oiliness agents, extreme pressure agents, rust inhibitors, oxidation inhibitors, corrosion inhibitors, viscosity index improving agents, detergents and dispersants.

The following examples illustrate lubricating oil compositions of this invention.

EXAMPLE 5

A mineral lubricating oil composition having an SUS viscosity in centistokes at 100° F. of 100 containing 1% by weight of 3-phenyl-6-tetrapropanyl-5,6-dihydrouracil.

EXAMPLE 6

A mineral lubricating oil composition having an SUS viscosity in centistokes at 100° F. of 150 containing 2 weight percent of 3-decyloxypropylaminopropyl-6-polyisobutenyl-(1200 MW)-5,6-dihydrouracil.

EXAMPLE 7

An SAE-20 mineral lubricating oil containing 1.5 weight percent of 3-phenyl-6-polyisobutenyl-(1290 MW)-5,6-dihydrouracil.

EXAMPLE 8

A mineral lubricating oil composition having an SUS viscosity in centistokes at 100° F. of 125 and at 200° F. of 12.3 containing 2.0 weight percent of zinc dialkyldithiophosphate, 1.75 weight percent of an overbased sulfurized alkylphenolate and 2% of 3-phenyl-6-polyisobutenyl-(300 MW)-5,6-dihydrouracil.

EXAMPLE 9

An ester base lubricating oil composition comprising a major portion of an aliphatic ester based oil formed from the reaction of pentaerylthritol and a mixture of organic monocarboxylic acids having 5 to 10 carbon atoms containing 2.0 weight percent of 3-phenyl-6-polyisobutenyl-(500 MW)-5,6-dihydrouracil.

EXAMPLE 10

An SAE-30 mineral lubricating oil containing 3 weight percent of 3-phenyl-6-ethylene-propylene copolymer(800 MW)-5,6-dihydrouracil.

EXAMPLE 11

An SAE-20 mineral lubricating oil containing 2 weight percent of the product of Example 4, 2.5 weight percent calcium sulfonate and 2% of an alkenyl succinimide derived from polyisobutenyl-(1290 MW) succinic acid anhydride and triethylenetetramine.

The property of the additive of the invention for modifying the deposits formed by a lubricating oil composition in an internal combustion engine was demonstrated in a bench test which correlates well with the Mack ENDT-675 Engine Test which is a modification of the Mack T-1 Diesel Piston Deposit Test. In the bench test, a burner nozzle is positioned midway inside a six-inch heat shielded well which rests on a hot plate as a source of heat. An aluminum panel is placed at the bottom of the well three inches below the vertically positioned downwardly directed nozzle. The surface temperature of the aluminum panel is controlled by a thermocouple.

In operation, the temperature of the aluminum panel is maintained at 680° F. The test oil is passed through the nozzle at a rate of 9 liters per minute in conjunction with an air jet. A deposits build-up forms on the aluminum panel over a run period of 2 hours duration. On completion of the high temperature oil oxidation run, the aluminum panel with the adhering oil deposits is cooled to room temperature. A segment of the adhering deposits on the disc was isolated by removal of adjacent deposits. The isolated segment covering a known area of the disc was then subjected to a shearing stress parallel to the disc face. The shearing tool was a flat metal specimen attached to the beam of a laboratory balance. Weights were added to the beam until the deposit segment was sheared off. The results expressed in grams measure the shearing force and permit a comparison of the adhesion/cohesion property of the deposits formed by the oil compositions.

The adhesion/cohesion property of three oil compositions containing the additive of the invention was determined in the following tests in comparison to oil compositions without the additive. Base Oil A was a solvent neutral oil of paraffinic character.

Commercial Oil B was a crankcase lubricating oil composition containing an overbased calcium sulfonate, a zinc dithiophosphate, a methacrylate VI improver and a conventional dispersant, antioxidant and foam inhibitor.

Commercial Oil C was a lubricating oil composition containing conventional additives including a calcium carbonate overbased calcium sulfonate, a zinc diisodecyldithiophosphate, a methacrylate pour depressant, an ashless dispersant, a dinonyldipenylamine antioxidant and a foam inhibitor. The inspection values for the above oils were as follows:

TABLE I

|  | Base Oil A | Commercial Oil B | Commercial Oil C |
|---|---|---|---|
| Gravity, API | 27.2 | 25.8 | 26.8 |
| SUS Viscosity, in cs. |  |  |  |
| at 100° F. | 183.3 | 125.4 | 124.6 |
| at 210° F. | 15.18 | 12.3 | 12.47 |
| TBN (Total Base Number) | — | 6.70 | 7.00 |
| Phosphorus, % | — | 0.17 | 0.19 |
| Calcium, % | — | 0.23 | 0.22 |
| Zinc, % | — | 0.10 | 0.10 |
| Sulfur, % | — | — | 0.64 |

The effect of the additive of the invention on the adhesion/cohesion properties of the deposits formed by the the oil compositions of the invention in the above-described test are set forth in the following table:

TABLE II

| Deposit Cohesive Test | | |
|---|---|---|
| Run | Composition | Deposit Cohesiveness Measurement (grams) |
| 1 | Base Oil A | 1500 |
| 2 | Base Oil A + 2 wt. % of Example 2 | 400 |
| 3 | Commercial Oil B | 1600 |
| 4 | Commercial Oil B + 2 wt. % of Example 2 | 600 |
| 5 | Commercial Oil C | 1100 |
| 6 | Commercial Oil C + 2 wt. % of Example 2 | 700 |

The foregoing tests demonstrate that the hydrocarbyl-substituted dihydrouracil compound of the invention was surprisingly effective for reducing the adhesive/cohesive properties of oxidized oil deposits formed from both conventionally formulated lubricating oil compositions and a base mineral oil that did not contain conventional lubricating oil additives.

I claim:

1. A hydrocarbyl-substituted dihydrouracil represented by the formula:

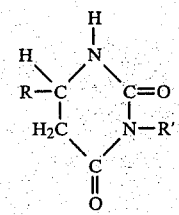

in which R is a hydrocarbyl radical having an average molecular weight ranging from about 150 to 2000, R' is hydrogen, a hydrocarbyl radical having from 1 to 20 carbon atoms or an R''—(X—R''')$_y$— radical in which R'' is an alkyl radical having from 1 to 12 carbon atoms, X is oxygen or an NH radical, R''' is a divalent hydrocarbyl radical having from 1 to 3 carbon atoms and y is an integer from 1 to 3.

2. A dihydrouracil according to claim 1 in which R has an average molecular weight ranging from about 800 to 1400.

3. A dihydrouracil according to claim 1 in which R' is hydrogen or a hydrocarbyl radical having from 1 to 12 carbon atoms.

4. A hydrocarbyl-substituted dihydrouracil represented by the formula:

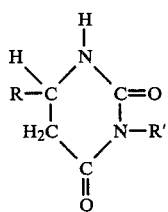

in which R is a polyalkenyl radical having an average molecular weight ranging from about 150 to 2000 and R' is hydrogen, an aryl or an alkaryl radical having from 6 to 10 carbon atoms.

5. A dihydrouracil according to claim 4 in which R is a polyalkenyl radical having an average molecular weight ranging from about 800 to 1400.

6. A dihydrouracil according to claim 4 in which R is a polyisobutenyl radical.

7. A dihydrouracil according to claim 4 in which R is an ethylene-propylene copolymer radical.

8. The compound 3-phenyl-6-polyisobutenyl-(300 MW)-5,6-dihydrouracil.

9. The compound 3-phenyl-6-polyisobutenyl-(1290 MW)-5,6-dihydrouracil.

10. The compound 3-phenyl-6-tetrapropenyl-5,6-dihydrouracil.

11. The compound 3-decyloxypropylaminopropyl-6-polyisobutenyl-(1290 MW)-5,6-dihydrouracil.

12. A method for preparing a 6-hydrocarbyl-substituted dihydrouracil which comprises reacting an N-hydroxy hydrocarbyl-substituted succinimide represented by the formula:

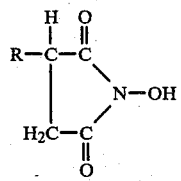

in which R is a hydrocarbyl radical having an average molecular weight ranging from about 150 to 2000, with p-toluenesulfonyl choride in the presence of an acid acceptor to produce an intermediate addition reaction product, and reacting said intermediate reaction product with an equimolar amount of a primary amine, said amine being represented by the formula:

R'NH$_2$ in which R' is hydrogen, a hydrocarbyl radical having from about 1 to 20 carbon atoms or an R''(X—R''')$_y$ radical in which R'' is an alkyl radical having from 1 to 12 carbon atoms, X is oxygen or an NH radical, R''' is divalent hydrocarbyl radical having from 1 to 3 carbon atoms and y is an integer from 1 to 3 to produce said 6-hydrocarbyl-substituted dihydrouracil.

13. A method according to claim 12 in which R is a polyisobutenyl radical.

14. A lubricating oil composition comprising a major proportion of a base oil of lubricating viscosity and from about 0.1 to about 5 percent by weight of a hydrocarbyl-substituted dihydrouracil represented by the formula:

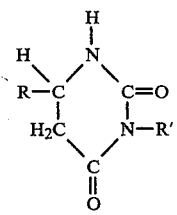

in which R is a hydrocarbyl radical having an average molecular weight ranging from about 150 to 2000, R' is hydrogen, a hydrocarbyl radical having from 1 to 20 carbon atoms or an R''—(X—R''')$_y$— radical in which R'' is an alkyl radical having from 1 to 12 carbon atoms, X is oxygen or an NH radical, R''' is a divalent hydrocarbyl radical having from 1 to 3 carbon atoms and y is an integer from 1 to 3.

15. A lubricating oil composition according to claim 14 in which R is a polyalkenyl radical.

16. A lubricating oil composition according to claim 14 in which said base oil is a mineral lubricating oil.

17. A lubricating oil composition according to claim 14 in which said dihydrouracil is a 3-phenyl-6-polyisobutenyl-5,6-dihydrouracil.

18. A lubricating oil composition according to claim 14 in which said dihydrouracil is 3-phenyl-polyisobutenyl (300 MW)-5,6-dihydrouracil.

19. A lubricating oil composition according to claim 14 in which said dihydrouracil is 3-phenyl-6-polyisobutenyl (1290 MW)-5,6-dihydrouracil.

20. A lubricating oil composition according to claim 14 in which said dihydrouracil is 3-phenyl-6-tetrapropenyl-5,6-dihydrouracil.

21. A lubricating oil composition according to claim 14 containing from about 0.1 to 5 weight percent of said hydrocarbyl-substituted dihydrouracil.

* * * * *